United States Patent [19]

Zair

[11] Patent Number: 5,798,498
[45] Date of Patent: Aug. 25, 1998

[54] METHOD AND APPARATUS FOR APPLYING LASER BEAMS TO A WORKING SURFACE, PARTICULARLY FOR ABLATING TISSUE

[75] Inventor: Eliezer Zair, Bnei Brak, Israel

[73] Assignee: Laser Industries, Ltd., Israel

[21] Appl. No.: 715,745

[22] Filed: Sep. 19, 1996

Related U.S. Application Data

[62] Division of Ser. No. 358,386, Dec. 19, 1994, Pat. No. 5,582,752.

[30] Foreign Application Priority Data

Dec. 17, 1993 [IL] Israel ............................... 108059

[51] Int. Cl.⁶ .................................................. B23K 10/00
[52] U.S. Cl. ........................ 219/121.83; 219/121.85; 219/121.79; 356/399; 356/153; 606/11
[58] Field of Search ..................... 219/121.85, 121.83, 219/121.79, 121.8, 121.62; 356/138, 139, 399, 153; 606/18, 2, 13, 9–12, 16

[56] References Cited

U.S. PATENT DOCUMENTS

| | | |
|---|---|---|
| 3,614,238 | 10/1971 | Stites ............................... 356/124 |
| 3,848,104 | 11/1974 | Locke . |
| 4,266,548 | 5/1981 | Davi . |
| 4,665,913 | 5/1987 | L'Esperance, Jr. . |
| 4,668,088 | 5/1987 | Quinque et al. ................... 356/138 |
| 4,733,660 | 3/1988 | Itzkan . |
| 4,780,590 | 10/1988 | Griner et al. . |
| 5,110,209 | 5/1992 | Elshoud et al. ................... 356/138 |
| 5,163,936 | 11/1992 | Black et al. ....................... 606/18 |
| 5,315,111 | 5/1994 | Burns et al. ....................... 250/235 |
| 5,364,391 | 11/1994 | Konwitz . |
| 5,411,502 | 5/1995 | Zair . |
| 5,474,549 | 12/1995 | Ortiz et al. . |
| 5,484,980 | 1/1996 | Pratt et al. . |

*Primary Examiner*—Mark H. Paschall
*Attorney, Agent, or Firm*—Cobrin Gittes & Samuel

[57] ABSTRACT

A method and apparatus applying a laser beam to a working surface, by displacing the laser beam to trace a plurality of circular scans over the working surface; and continuously varying the diameters of the circular scans at a rate to produce a substantially homogenous distribution of the laser energy over the working surface.

8 Claims, 6 Drawing Sheets

$Vo_3 < Vo_2 < Vo_1$

METHOD AND APPARATUS FOR APPLYING LASER BEAMS TO A WORKING SURFACE, PARTICULARLY FOR ABLATING TISSUE

This is a Division of application Ser. No. 08/358,386, filed Dec. 19, 1994, now U.S. Pat. No. 5,582,752.

FIELD AND BACKGROUND OF THE INVENTION

The present invention relates to a method and apparatus for applying a laser beam to a working surface. The invention is particularly useful in a surgical laser for the removal of undesired tissue by ablation, and is therefore described below with respect to this application.

When removing undesired tissue by ablation with the use of a laser beam, the follow criteria should be maintained: (1) minimal thermal damage to the surrounding tissue; (2) avoidance of char residue over the ablated area; and (3) uniform ablation of the tissue without causing holes or cracks in the surrounding tissue.

To fulfill criteria (1) and (2), a laser power density of 40 W/mm$^2$ on tissue, and a lasing duration of one millisecond, should be maintained so that the energy density will reach a level of 40 MJ/mm$^2$. Under these conditions, the char residue heats up to a temperature of over 500°, whereupon it is oxidized and converted to gas. The high power density ablates tissue at such a rapid rate, that thermal damage does not permeate a depth of more than 100 µm, therefore achieving minimal thermal damage.

To fulfill criterion (3), a beam with a diameter of at least 3.5 mm (area of 10 mm$^2$) should be used. A smaller beam diameter will cause holes and cracks in the tissue.

In order to maintain a power density of 40 W/mm$^2$ over an area of 10 mm$^2$, a 400 W laser is required. A medical laser of such power levels is both too large in size and too expensive. Alternatively, a low-powered focused laser beam may be used with the beam scanning an area of 10 mm$^2$ with relatively high velocity.

It has been previously proposed to displace the laser beam to trace a circular scan over the working surface (e.g., published European Patent Application 0172490), but the scanned area is thus limited to an annular ring. It has also been proposed to scan larger areas by Lisajou patterns, but the Lisajou patterns so formed are such that the velocity of scanning at the center of the area is much smaller (e.g., thirty times smaller) than the velocity on the perimeter. Low scanning velocity in the center causes the beam to linger at the center, thus causing a higher ablation rate in the center than on the perimeter.

OBJECTS AND BRIEF SUMMARY OF THE INVENTION

An object of the present invention is to provide a method, and also apparatus, of applying a laser beam to a working surface such as to produce a substantially homogenous distribution of the laser energy over the working surface.

According to one aspect of the present invention, there is provided a method of applying a laser beam to a working surface, comprising: displacing the laser beam to trace a plurality of circular scans over the working surface; and continuously varying the diameters of the circular scans at a rate to produce a substantially homogenous distribution of the laser energy over the working surface.

According to further features in the preferred embodiments of the invention described below, the laser beam is displaced to trace the circular scans by deflecting the laser beam along two orthogonal axes by first and second deflector devices having axes perpendicular to each other, the deflector devices being oscillated by first and second motors operated at a phase difference of 90°. In the described preferred embodiment, the laser beam is of circular cross-section, and the minimum diameter of the circular scans is approximately equal to the diameter of the laser beam. Preferably, the diameter is at least 3.5 mm. The diameters of the circular scans are varied so that they partially overlap the same amount.

As will be described more particularly below, the diameters may be continuously varied to produce the substantially homogenous distribution of the laser energy by varying the frequency of oscillation, maximum value of voltage, or both frequency of oscillation and maximum value of voltage, of the deflector devices.

According to a further feature in a preferred embodiment of the invention described below, the laser beam is applied via an endoscope to the working surface. In such a case, the novel method of applying the laser beam permits easy determination, and correction, of any misalignment between the laser beam and the endoscope.

More particularly, according to another aspect of the present invention, there is provided a method of checking the alignment of a radiant energy beam with respect to the inlet end of a tubular member, comprising: reciprocating the radiant energy beam along a first othogonal axis while observing the trace of the radiant energy beam at the output end of the tubular member; and reciprocating the radiant energy beam along a second orthogonal axis while observing the trace of the radiant energy beam at the output end of the tubular member; a curved non-linear configuration of the ends of the observed trace indicating misalignment of the laser beam with the endoscope, whereas a straight co-linear configuration of the ends of the observed trace indicating no misalignment of the laser beam with the endoscope.

The invention also provides apparatus for applying a laser beam in accordance with the above method.

As will be shown more particularly below, the described method and apparatus enable homogenous scanning of the entire working surface such as to make the method and apparatus particularly useful for the surgical removal of tissue by ablation while causing minimal thermal damage to the surrounding tissue, holes or cracks in the surrounding tissue, or char residue over the ablated area.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
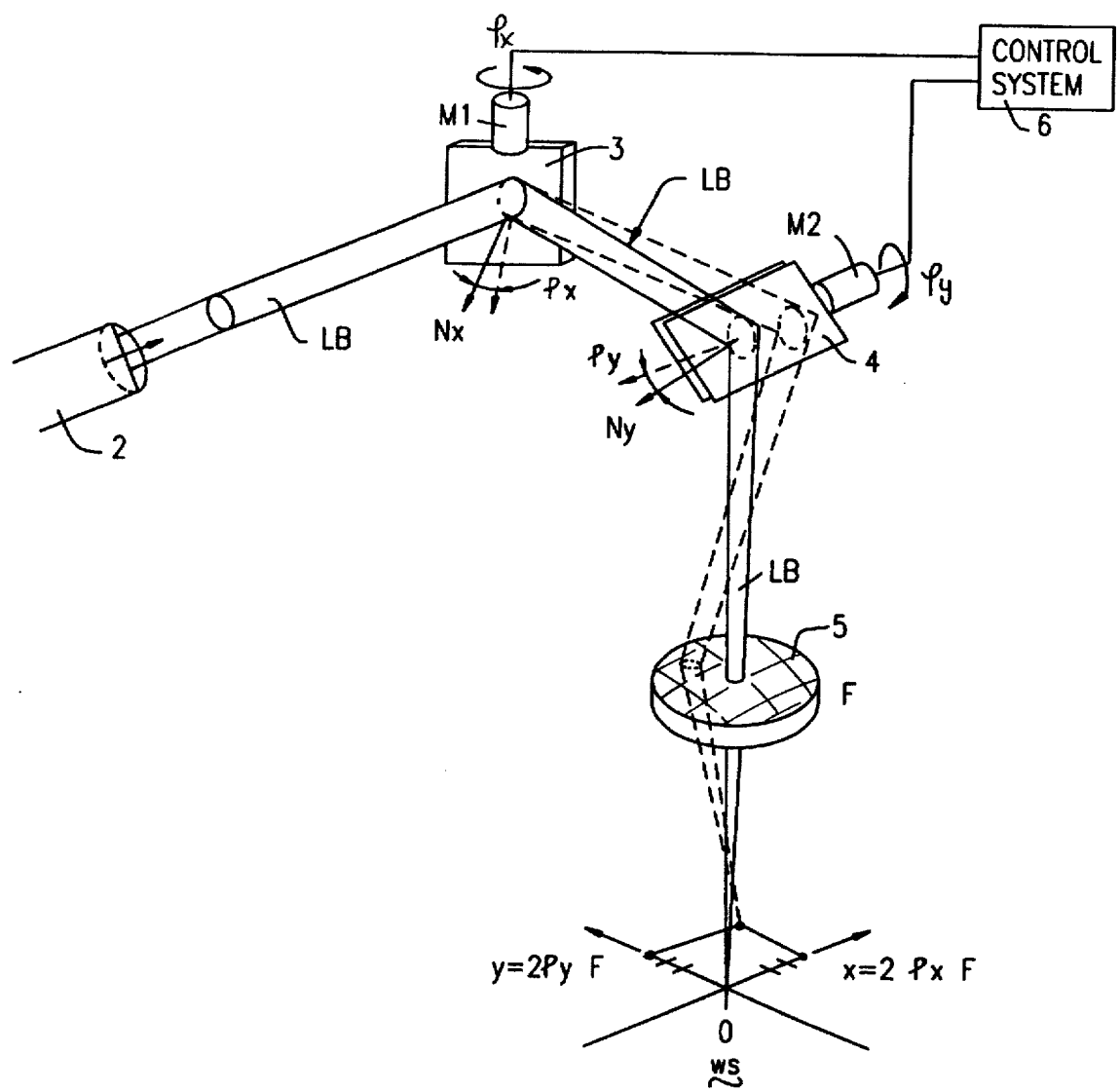
FIG. 1 illustrates one form of apparatus constructed in accordance with the present invention.

The apparatus illustrated in FIG. 1 includes a laser 2 outputting a laser beam LB which is directed to a working surface WS, such as tissue to be surgically removed by ablation. The laser beam LB from laser 2 is first deflected by a mirror deflector device 3, then by a mirror deflector device 4, which directs the beam via a focusing lens 5 to the working surface WS. Mirror 3 is oscillated along one axis, e.g., the X-axis, by a first motor $M_1$; and mirror 4 is oscillated along the other orthogonal axis, e.g., the Y-axis, by a second motor $M_2$. The two mirrors 3, 4, are located such that their axes (their normals Nx, Ny) are perpendicular to each other. Both motors are controlled by a control system, generally designated 6, in a manner to produce a homogenous scanning of the laser beam LB over the working surface WS, namely the tis sue to be ablated.

The following description, with reference particularly to FIGS. 2–8, will explain how the motors $M_1$, $M_2$ are controlled to produce a homogenous scanning of the tissue to be ablated.

Figure 2:
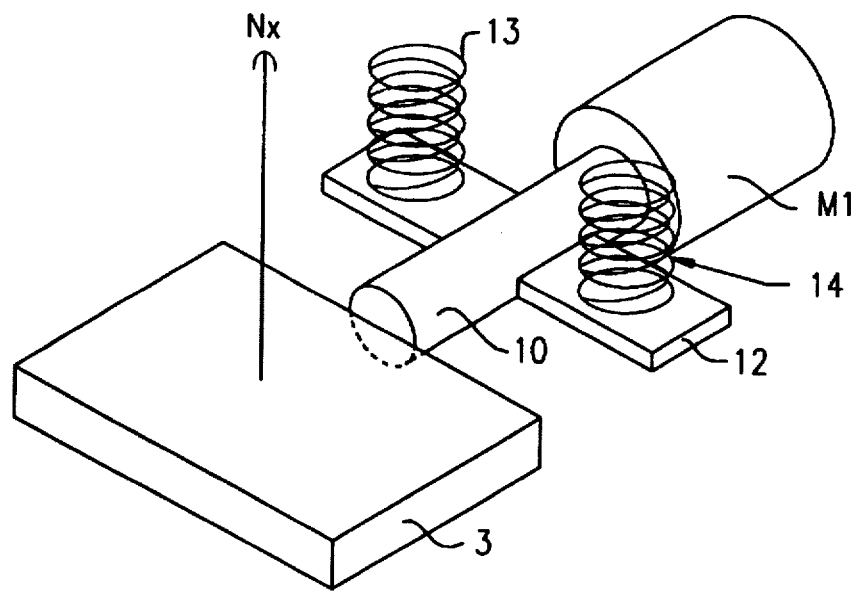
FIGS. 2–8 are diagrams helpful in explaining the operation of the apparatus of FIG. 1.

FIG. 2 illustrates one of the oscillating mirrors, e.g., mirror 3, and its motor drive, e.g., motor $M_1$. Motor $M_1$ is connected via its rotary shaft 10 to mirror 3. The mirror's normal vector Nx is perpendicular to axis 10. Two arms 11, 12 are connected to axis 10 and press against two springs 13, 14, which are connected to the motor's housing. The two springs 13, 14 produce opposite torques on the motor's shaft 10, so that the shaft is at angular equilibrium.

When the motor $M_1$ is supplied with an electrical voltage V, it rotates the mirror 3 against the springs 13 14 until a new equilibrium is reached at a new angle ρ in relation to the previous equilibrium point (ρ=0). A minus voltage (−V) will cause the motor and the mirror to rotate in the opposite direction at an angle of −ρ. When the rate of voltage change is slow compared to the resonance frequency of the system, the anglular dispalcement is linear to V; that is:

$$\rho = \alpha V \qquad \text{Eq. (1)}$$

where α is a proportional factor which is determined by the springs constants and the motor power.

When feeding the motor with alternatng voltgage, as described in the following equation:

$$V(t) = V_o \sin(2\pi ft) \qquad \text{Eq. (2)}$$

where $V_o$ is the maximum value of voltage, f the frequency, and t is the time; the motor, together with the mirror, oscillates clockwise and counterclockwise according to the equation:

$$\rho(t) = \rho(V_o, f) \sin(2\pi ft + \Phi) \qquad \text{Eq. (3)}$$

where $\rho(V_o, f)$ is the maximum displacement angle, which depends on $V_o$ and the frequency f; and Φ is the phase between the mechanical oscillations and the electrical voltage.

Figure 3:
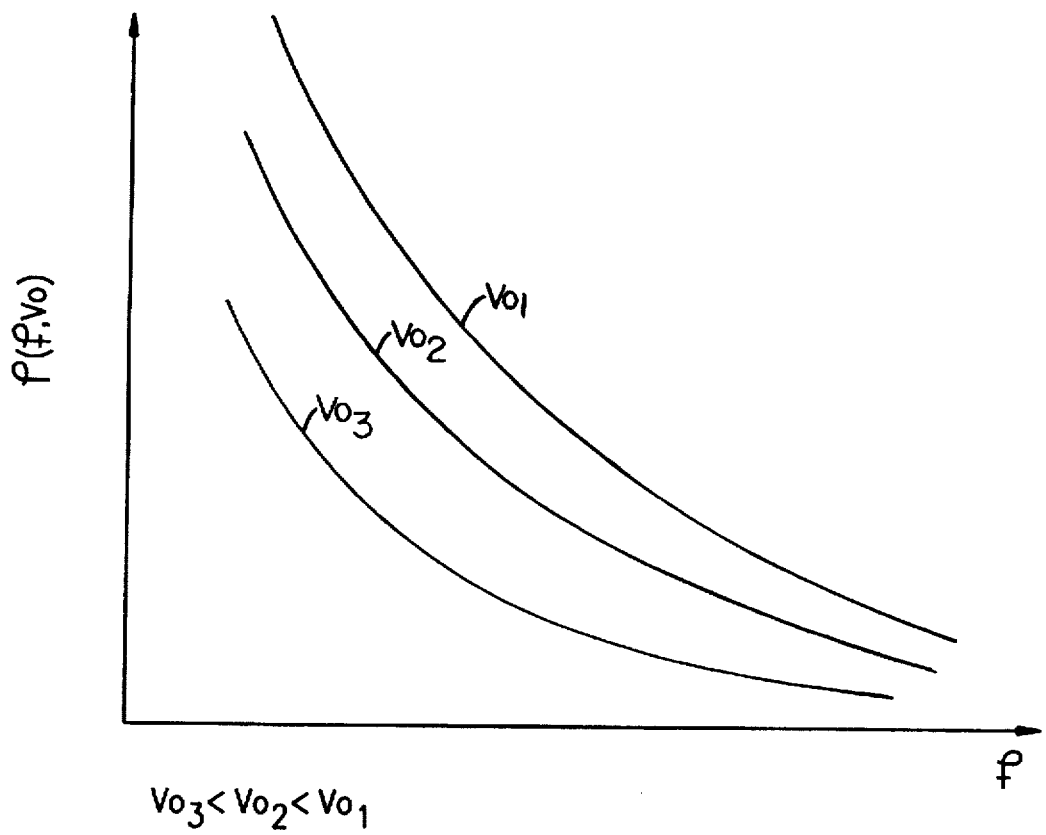

When using frequencies f, which are greater than the resonance frequency of the system, the maximal displacement angle $\rho(V_o, f)$ can be described as a function of f and $V_o$ (see FIG. 3).

Each of the functions ρ(f) in FIG. 3 is ascribed to a different $V_o$. An increase in $V_o$ will cause an increase in displacement amplitude. The variation of the displacement amplitude may be controlled by one of the following methods:

1. Keep $V_o$ constant and vary f;
2. Keep f constant and vary $V_o$; or
3. Vary both $V_o$ and f.

Figure 4:
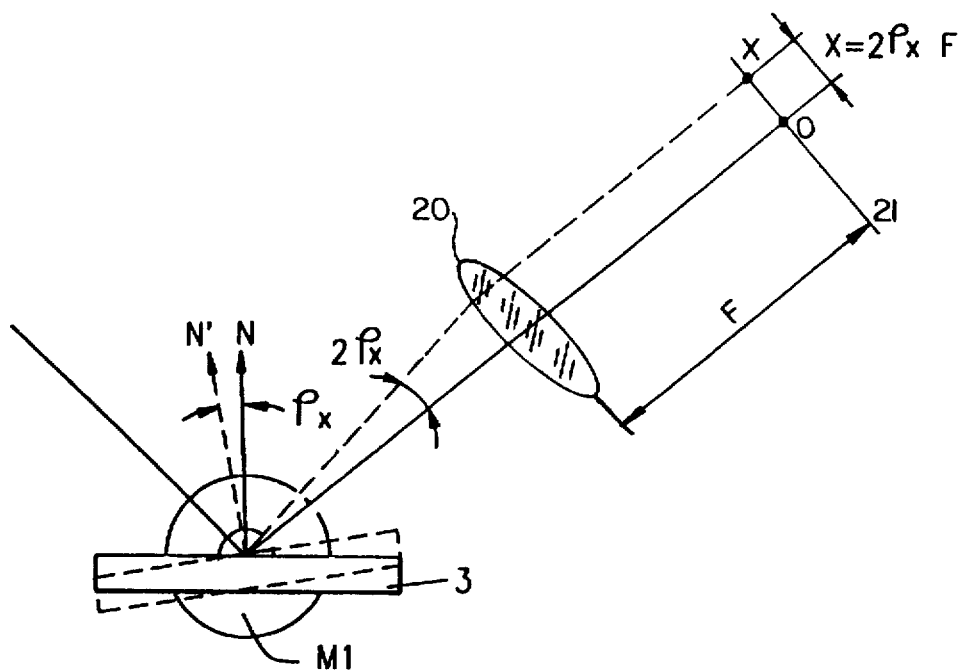
Figure 5:
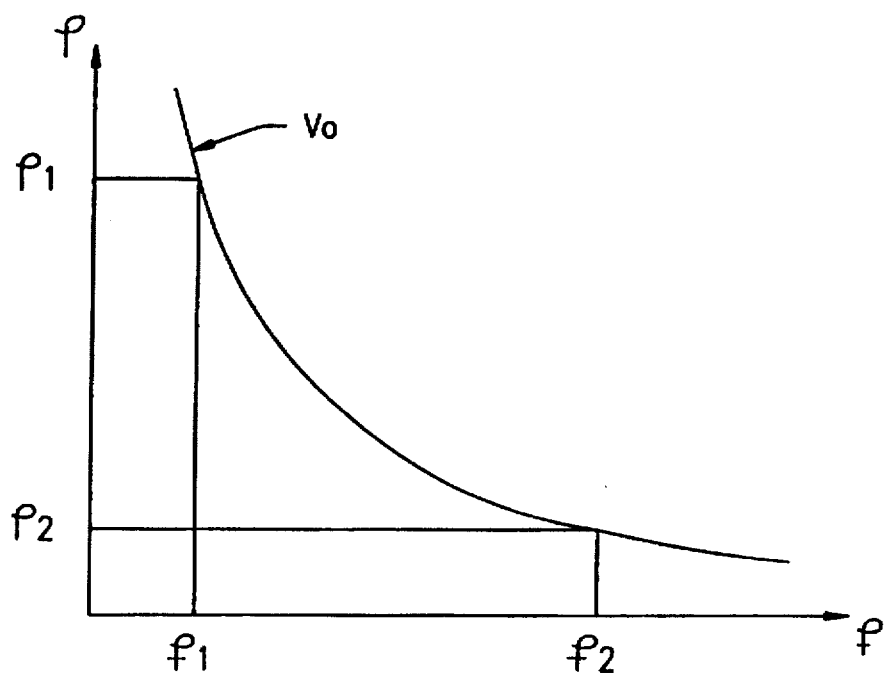

FIG. 4 illustrates the deflection of a light beam by the scanner. When a light beam strikes mirror 3 at an angle of 45°, the beam is reflected and returned at an angle of 45°. If a lens 20 with a focal length of F is placed in the beam path, the beam will focus at a point O on the focal plane 21. This point O is referred to as the origin of the axis. When the mirror rotates at an angle of $\rho_x$, the returned beam is reflected at an angle of 2 $\rho_x$ and focused on the focal plane at point X, which is given by:

$$X = 2\rho_x F \qquad \text{Eq. (4)}$$

When the two scanners are placed so that the two mirror normals Nx, Ny are perpendicular as shown in FIG. 1, voltage supplied to the two motors ($M_1$, $M_2$) will cause movement at the focal plane in both x and y directions as follows:

$$X = 2\rho_x F$$
$$Y = 2\rho_y F \qquad \text{Eq. (5)}$$

If the motors are provided with an alternating voltage at a frequency f and an amplitude $V_o$, but with a phase difference of 90°, then:

$$V_x = V_o \sin(2\pi ft)$$
$$V_y = V_o \qquad \text{Eq. (6)}$$

After substituting in Equations (3) and (5), the coordinates will be as follows:

$$x(t) = 2F (V_o, f) \sin(2\pi ft)$$
$$y(t) = 2F (V_o, f) \cos(2\pi ft) \qquad \text{Eq. (7)}$$

These equations form a circle with a radius of:

$$r = \sqrt{x^2 + y^2} = \sqrt{8F} \; \rho(V_o, f) \qquad \text{Eq. (8)}$$

The velocity on the circumference will be $$V(r) = 2\pi f r = \sqrt{32} \; \pi F f \, \rho(V_o, f) \qquad \text{Eq. (9)}$$

The velocity is constant for the circumference.

The radius of the scanning can be controlled by changing $\rho(V_o, f)$. This can be done by: (1) varying f when $V_o$ is constant, (2) by varying $V_o$ when f is constant, or (3) by varying both.

Figure 6:
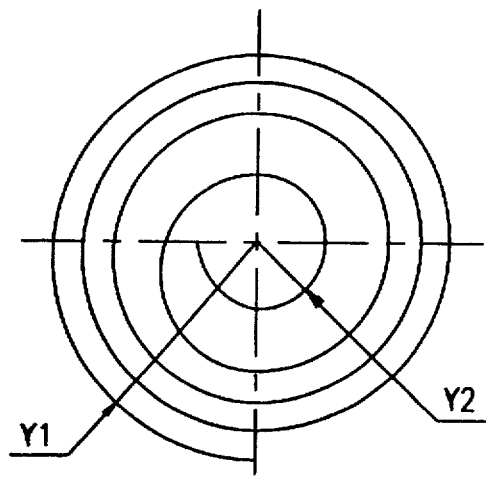
Figure 7:
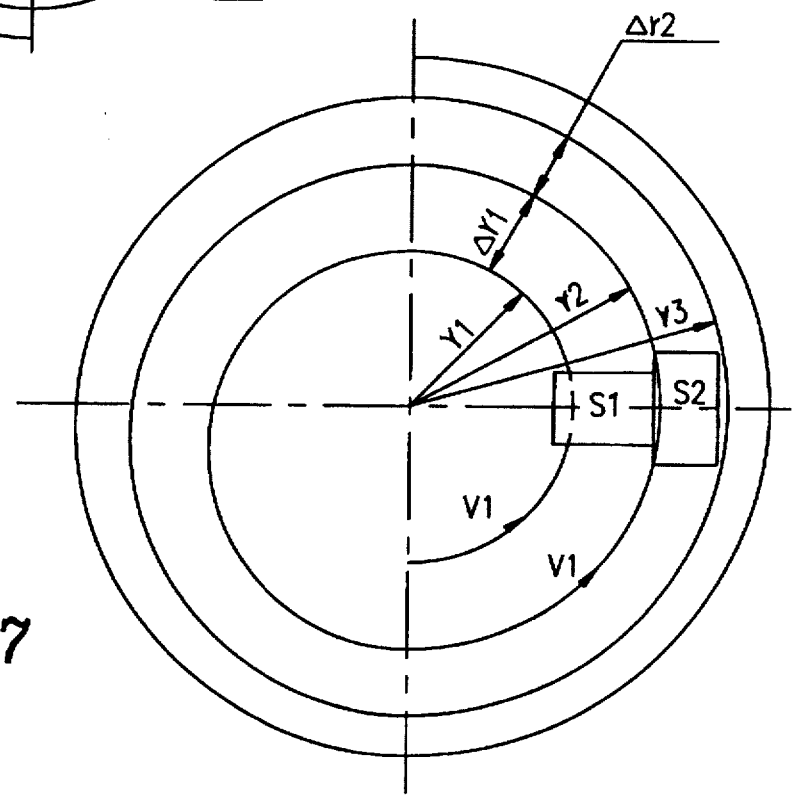

To scan a full area (not just the perimeter), a constant voltage amplitude $V_o$ with a curve described in FIG. 6 may be supplied to the two motors. Operating the motors at a frequency $f_1$ will cause rotational amplitude $\rho_1$ and circular scanning according to Equation (8) at a radius of $r_1 = \sqrt{8} \, F \, \rho_1(V_o, f_1)$. Gradually increasing the frequency to $f_2$ will cause the rotational amplitude to gradually decrease to the value $\rho_2(V_o, f_2)$ and the radius of the circular scanning to $r_2 = \sqrt{8} \, F \, \rho_2(V_o, f_2)$ where $r_2 < r_1$.

On the focal plane, circles are formed with gradually decreasing radii from $r_1$ to $r_2$, thereby covering an area of a ring with an outer radius of $r_1$ and an inner radius of $r_2$ (see FIG. 6). Gradually decreasing the frequency to $f_1$ will produce an area scanning with circles of gradually incrasing radii to a radius of $r_1$. Alternately varying frequencies between $f_1$ and $f_2$ will cause area scanning by means of continuously increasing and decreasing circles. The boundaries of the scanning (outer and inner radii) are determined by the extreme values of frequencies, $f_1$ and $f_2$. The control system 6 (FIG. 1) can be easily computerized such that the user selects the diameter of scanning, and the system determines the required frequencies according to the above equations.

Since the difference between two following scanning radii decreases, the energy per unit area increases. The difference between two consecutive scanning radii can be controlled by the rate of change of f. Since the frequency f is increased or decreased for each circular scanning, the difference between two consecutive circles will increase or decrease. Controlling the rate that frequency f is changed throughout each scanning, enables the control of radial energy distribution.

Figure 8:
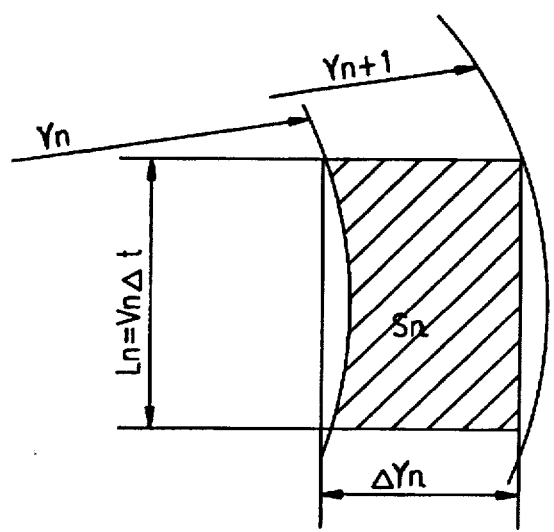

The scanned area is described in FIG. 8. $S_1$ and $S_2$ represent block areas. The area width always is the difference of radii between two consecutive scannings, and their height is the displacement L that the beam has traversed at unit time $\Delta t$. The displacement will be:

$$L = V(r) \Delta t \qquad \text{Eq. (10)}$$

wherein:

P=laser power

E=energy radiated onto block area S $r_n$=radius of scanning corresponding to $S_n$ $\Delta r_n$=the difference between $r_n$ and the consecutive radius $r_{n+1}$ ($\Delta r_n = r_{n+1} - r_n$)

V(r)=linear velocity of the scanning beam $\Delta t$=time unit determined for all areas $L_n$=height of th block area corresponding to $r_n$ σ=energy density per unit time in a block area corresponding to radius $r_n$ The energy density may be calculated as follows:

$$\sigma_n = \frac{E}{S_n} = \frac{E}{L_n \cdot \Delta r_n} = \frac{P\Delta t}{V(r_n) \cdot \Delta t \cdot \Delta r_n} = P \frac{1}{V(r_n)\Delta r_n} \qquad \text{Eq. (11)}$$

Assuming that the laser power is constant throughout scanning, the power density per unit area is proportional to $1/V(r_n) \cdot \Delta r_n$. To achieve constant energy density for the entire scanning area (homogenous ablation), $V(r_n) \cdot \Delta r_n$ should be kept constant. From Equation 9:

$$f_n = \rho(V_o, f_n) \cdot r_n = \text{CONSTANT} \qquad \text{Eq. (12)}$$

Following is one procedure for producing a constant energy density wherein the frequency of the two motors $M_1$, $M_2$ is controlled by the control system 6 (FIG. 1). The minimum diameter of the circular scans is equal to the diameter of the light beam LB, which is preferably at least 3.5 mm; and the diameters of the circular scans are varied such that they partially overlap the same amount:

1) The minimum radius $r_2$ is determined for the first scanning circle, according to the radius of the focused laser beam.

2) The first radii difference $\Delta r_1$, between the first and second scanning circles, is determined at a value of ¾ of the radius of the focused laser beam, so that the scanning circles overlap.

3) A curve $\rho(V_o, f)$ is determined by selecting $V_o$. From this curve, frequency $f_1$ which corresponds to $r_1$, and frequency $f_2$ which corresponds to $r_2 = r_1 + \Delta r_1$, are chosen.

4) The product $C = \rho(V_o, f) \cdot \Delta r_1 f_1$ is calculated (Equation 12).

5) $\Delta r_2$ is calculated from Equation 12 $\Delta r_2 = C/\rho(V_o, f_2) \cdot f_2$.

6) The new radius is $r_3 = r_2 + \Delta r_2$, and $f_3$ is chosen from the curve.

7) $\Delta r_3$ is calculated $\Delta r_3 = C/\rho(V_o, f_3)f_3$, and so on until the outer radius is reached.

The sequence of frequencies (or matching time periods) in a phase difference of 90° are supplied by the control system 6 in FIG. 1 to the two motors $M_1$, $M_2$, thereby producing area scanning with uniform energy density for the entire area scanned.

Power density may also be controlled by varying $V_o$ and keeping f constant, or by varying both. Any desired radial energy distribution may be programmed except for constant radial energy distribution.

An important use of laser radiation in medicine is in the application of laser beams through different tube-like endoscopes. One of the common problems in using long narrow endoscopes is centering the laser beam with respect to the endoscope axis. When a laser beam is projected in a direction which is not perfectly parallel to the endoscope inner walls and is reflected, sometimes a number of times. Because of these reflections, the beam defocuses, and part of the beam power is absorbed by the endoscope walls and is lost, thereby lowering beam quality.

Figure 9:
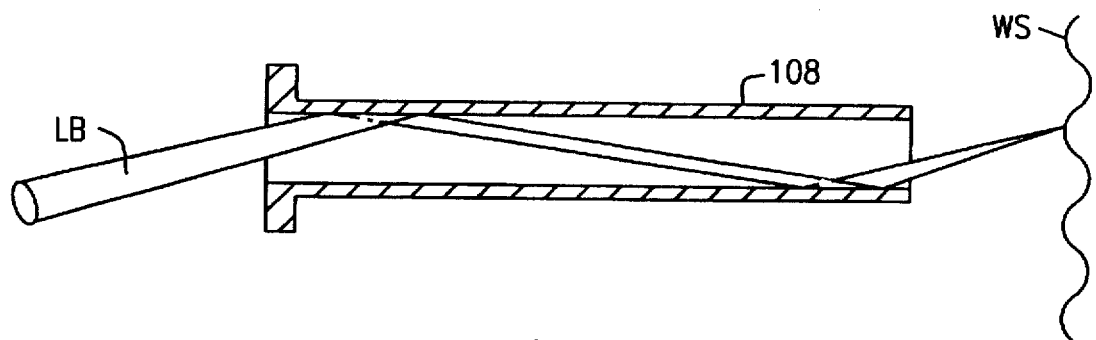
FIGS. 9, 10 and 11 are diagrams helpful in explaining an alignment advantage achievable by the invention.

Generally, it is difficult to ascertain whether or not the beam has traversed through the endoscope without reflection from the endoscope inner walls thereby lowering laser beam qualtity. A major difficulty in determining this is because, as shown in FIG. 9, a beam LB with a circular cross-section remains, after reflection from an endoscope 108, with almost the same circular cross-section. This makes alignment difficult to determine as compared to a beam with a linear cross-section.

Figure 10:
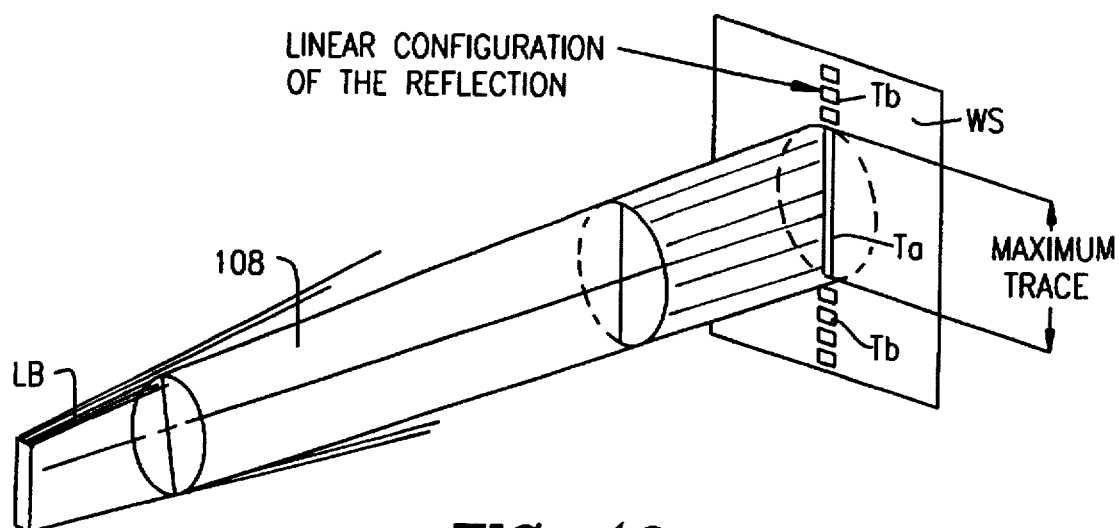
Figure 11:
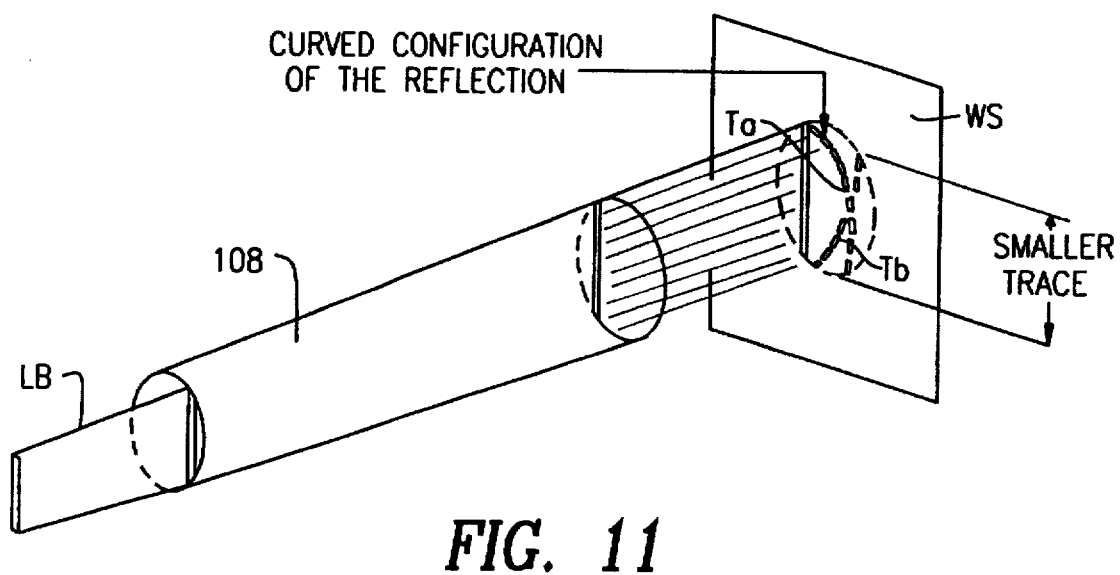

Thus, as shown in FIGS. 10 and 11, when a linearly cross-section beam LB is reflected from the inner surface of an endoscope 108 (or other tubular member), it is easy to distinguish in the trace T (a) the part of the beam that passes through the endoscope without reflection (indicated as trace Ta in FIGS. 10 and 11), and (b) the part of the beam that is reflected from the endoscope walls (indicated by traces Tb of weaker intensity than trace Ta). The relation of the traces Tb to the trace Ta shows the nature of the alignment between the beam axis and the endoscope axis. Hence, the greater the alignment between the beam axis and the endoscope axis, the more co-linear are the traces Tb with respect to the trace Ta. FIG. 10 illustrates a precise alignment wherein traces Tb are precisely co-linear with trace Ta, whereas FIG. 11 illustrates a misalignment wherein traces Tb are curved to form a somewhat "banana" configuration with trace Ta.

The above-method of the present invention is particularly useful for applying laser beams through endoscopes since the method conveniently permits checking the alignment of the laser beam with the longitudinal axis of the endoscope, and correcting for any misalignment that may be present. The manner of doing this is described below particularly with reference to FIG. 12 which illustrates a laser apparatus as described in FIG. 1, except that it includes an endoscope 108 through which the laser beam LB is delivered to the working surface WS, such as tissue to be ablated.

Figure 12:
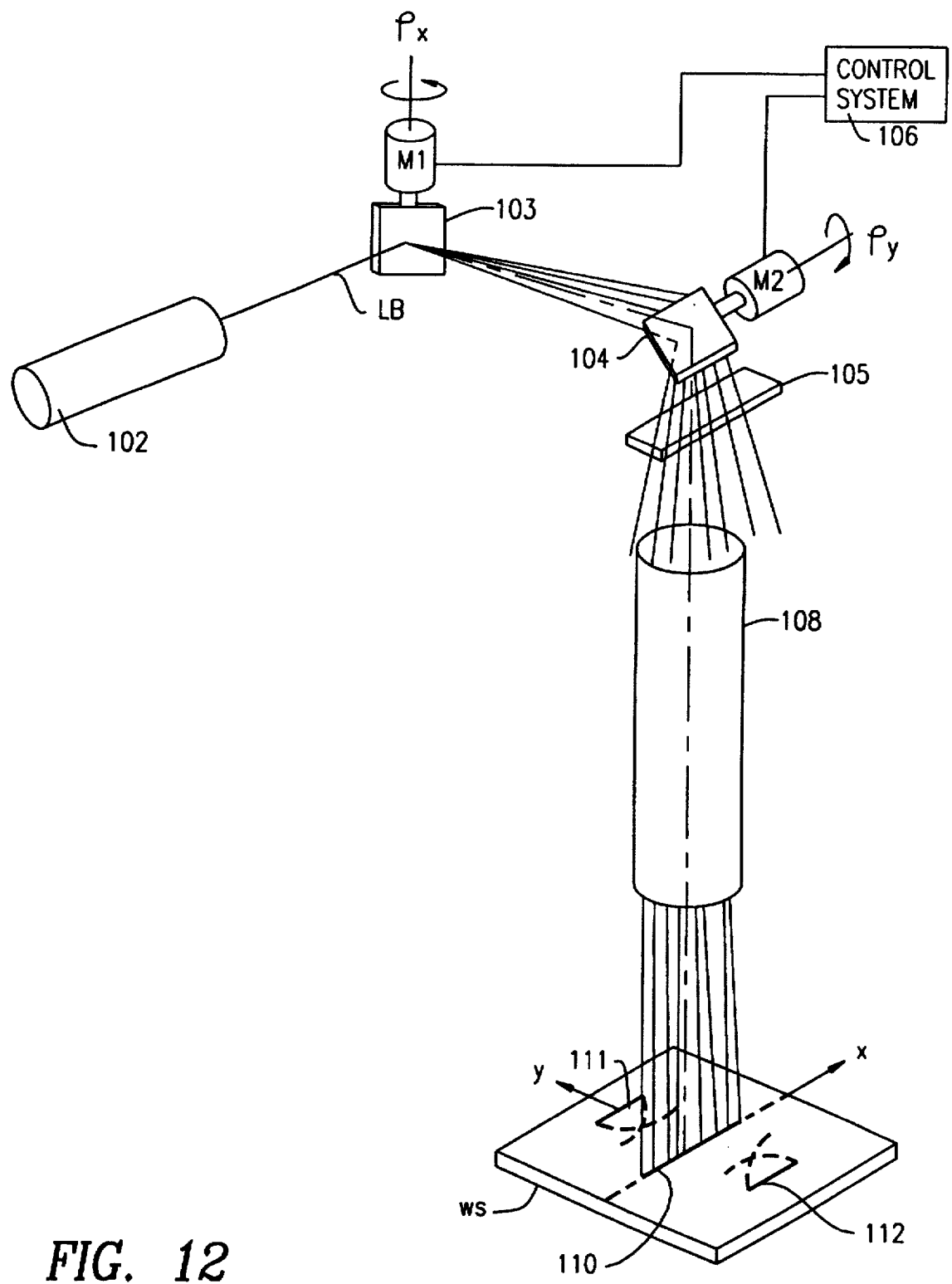
FIG. 12 illustrates a second form of apparatus constructed in accordance with the present invention to achieve the alignment advantages described in FIGS. 9–11.

Thus, the apparatus illustrated in FIG. 12 includes a laser 102 outputting a laser beam LB which is first deflected by a mirror 103 oscillated by a motor $M_1$ along the X-axis, and then deflected by a second mirror 104 oscillated by a motor $M_2$ along the Y-axis, before being delivered to the working surface WS via an optical system 105 (which includes the focusing lens 5 of FIG. 1), and an endoscope 108. As in FIG. 1, the two motors $M_1$, $M_2$ are controlled by a control system 106 in the same manner as described with respect to FIG. 1 to produce a homogenous scanning of the entire ablated area on the working surface WS.

Misalignment between the axis of the endoscope 108 and laser beam LB may arise because of the following causes:

1) misalignment between the endoscope and the laser delivery system caused by the mechanical tolerance of the connection; or 2) misalignment between the laser beam and the delivery system caused by tolerances in the optical system of the delivery system.

These misalignments combine vectorially to an overall deviation of the laser beam from the endoscope axis. In the scanner illustrated in FIG. 12, the overall angular error may be taken in the $\rho_x$ and $\rho_y$ components. Supplying the two motors $M_1$, $M_2$ with corresponding DC voltages $V_x$ and $V_y$, will rotate the mirrors 103, 104 by the angles $-\rho_x/2$ and $-\rho_y/2$, thus eliminating the angular error. The laser beam will enter the endoscope parallel to the endsocope axis.

Following is one procedure which may be used for checking the alignment of the laser beam LB with the endoscope 108, and for correcting any misalignment:

Stage 1

Motor $M_1$ is controlled by control system 106 to divert the beam in direction X. When the motor is supplied with alternating voltage at a constant frequency and amplitude, the laser beam LB is dispersed to form a linear projection in direction X. A part of the dispersed beam enters the endoscope 108. After exiting the endoscope, the beam strikes the target plane WS. If the dispersed beam is parallel in the direction Y to the endoscope axis, a straight line 110 of maximum length will form on the target plane. If the dispersed beam is not parallel to the endoscope axis, a shorter line with "banana" shape reflections 111 or 112 will form on the target area.

The user then controls system 106, e.g., by operating an electrical push-button, to supply motor $M_2$ with a DC voltage that gradually varies from $-V_2$ to $+V_2$. Mirror 104 rotates from an angle of $\rho_2/2$ to $+\rho_2/2$, which diverts the beam in the Y direction from an angle of $-\rho_2$ to $+\rho_2$. The angle $\rho_2$ is chosen so that it is larger than the maximal error between the laser beam and the endoscope axis. The user will see the beam scanning the target plane from position 111 to position 110 (or from position 112 to position 110). When the beam reaches position 110, forming a straight line of maximum length, the user releases the push-button and the system computer records the voltage $V_{yo}$ that diverted the beam in the endoscope Y direction.

Stage 2

Motor $M_2$ that diverts the beam in direction Y is supplied by control system 106 with an alternating voltage which creates a linearly dispersed beam in the direction Y. Motor $M_1$ is supplied with a gradually varying DC voltage, e.g., by pressing a push-button. When the dispersed beam forms a straight line of maximum length, the user releases the push-button and the system records the voltage $V_{xo}$ that diverted the beam in the endoscope direction X.

Stage 3

The user then switches to the area scanning mode, during which the control system 106 supplies the motors $M_1$, $M_2$ with the sequence of frequencies required for the area scanning. In addition to these frequencies, the system provides motor $M_1$ with DC voltage $V_{xo}$, and motor $M_2$ with DC voltage $V_{yo}$, such that the scanning area will center parallel to the endoscope axis.

While the invention has been described with respect to preferred embodiments, it will be appreciated that these are set forth merely for purposes of example, and that many variations, modifications and other applications of the invention may be made.

I claim:

1. A method of checking the alignment of a radiant energy beam with respect to the inlet of a tubular member by viewing an observable trace resulting from the energy beam passing through the tubular member, comprising:

a) reciprocating the radiant energy beam along a first orthogonal axis;

b) reciprocating the radiant energy beam along a second orthogonal axis; and c) coordinating steps (a) and (b) such that a curved non-linear configuration of the observed trace, indicating a misalignment of the radiant energy beam with respect to the inlet end of the tubular member, becomes linear, indicating an absence of said misalignment.

2. The method according to claim 1, wherein said tubular member is an endoscope.

3. An apparatus for checking the alignment of a radiant energy beam with respect to a tubular member, comprising:

a source for producing a radiant energy beam;

first means for reciprocating the radiant energy beam along a first orthogonal axis;

second means for reciprocating the radiant energy beam along a second orthogonal axis; and said first means and said second means positioned with respect to each other for producing at least one observable trace from said radiant energy beam with respect to the tubular member, said first means and said second means being adjustable with respect to each other such that a curved non-linear configuration of the ends of the observable trace, indicating misalignment of the beam with the tubular member, can be made into an observable trace with straight co-linear configurations of the ends, indicating an absence of said misalignment of the beam with respect to the tubular member.

4. The apparatus according to claim 3, wherein said source of said radiant energy beam is a laser outputting a laser beam.

5. The apparatus according to claim 3, wherein said tubular member is an endoscope.

6. An apparatus for checking the alignment of a radiant energy beam with respect to a tubular member, comprising:

a source for producing a radiant energy beam;

a tubular member through which the radiant energy beam is applied;

a scanner, said scanner including:

first means for reciprocating the radiant energy beam along a first orthogonal axis and;

second means for reciprocating the radiant energy beam along a second orthogonal axis, said tubular member, said first means and said second means positioned so as to produce at least one observable trace of said radiant energy beam with respect to the tubular member, said first and second means being adjustable so that a curved non-linear configuration of the ends of the observable trace that indicates misalignment of the beam with the tubular member, can be made into an observable trace with straight co-linear configurations of the ends of the observable trace, to indicate an absence of said misalignment of the beam with respect to the tubular member.

7. The apparatus according to claim 6, wherein said source of the radiant energy beam is a laser outputting laser beam.

8. The apparatus according to claim 6, wherein said tubular member is an endoscope.

* * * * *